US012718956B2

(12) United States Patent
Hayashi et al.

(10) Patent No.: US 12,718,956 B2
(45) Date of Patent: Aug. 25, 2026

(54) PATHWAY ANALYSIS APPARATUS, PATHWAY ANALYSIS METHOD, AND PATHWAY ANALYSIS PROGRAM

(71) Applicant: FRONTEO, Inc., Tokyo (JP)

(72) Inventors: Kazumi Hayashi, Tokyo (JP); Hiroyoshi Toyoshiba, Tokyo (JP); Yuna Takagi, Tokyo (JP); Miyuki Sakai, Tokyo (JP); Makoto Miyamoto, Tokyo (JP); Hironori Mitsuke, Tokyo (JP)

(73) Assignee: FRONTEO, Inc., Tokyo (JP)

( * ) Notice: Subject to any disclaimer, the term of this patent is extended or adjusted under 35 U.S.C. 154(b) by 73 days.

(21) Appl. No.: 18/580,834

(22) PCT Filed: Jun. 27, 2023

(86) PCT No.: PCT/JP2023/023755
§ 371 (c)(1),
(2) Date: Jan. 19, 2024

(87) PCT Pub. No.: WO2025/004167
PCT Pub. Date: Jan. 2, 2025

(65) Prior Publication Data
US 2025/0226112 A1 Jul. 10, 2025

(51) Int. Cl.
*G16H 50/50* (2018.01)

(52) U.S. Cl.
CPC .................................. *G16H 50/50* (2018.01)

(58) Field of Classification Search
CPC ........ G16H 50/30; G16H 50/20; G16H 50/50; G16H 50/70
See application file for complete search history.

(56) References Cited

U.S. PATENT DOCUMENTS

| | | | | |
|---|---|---|---|---|
| 2006/0004706 | A1 | 1/2006 | Tomioka et al. | |
| 2007/0022182 | A1 | 1/2007 | Ihara et al. | |
| 2025/0182844 | A1* | 6/2025 | Kain | G16B 40/20 |

FOREIGN PATENT DOCUMENTS

| | | | | |
|---|---|---|---|---|
| WO | 2003077159 A1 | 7/2005 | | |
| WO | 2005096207 A1 | 10/2005 | | |
| WO | WO-2024102200 A1 * | 5/2024 | | C12Q 1/6883 |

OTHER PUBLICATIONS

Shu, Zixin, et al. "Symptom-based network classification identifies distinct clinical subgroups of liver diseases with common molecular pathways." Computer methods and programs in biomedicine 174 (2019): 41-50. (Year: 2019).*

(Continued)

*Primary Examiner* — Constantine Siozopoulos
(74) *Attorney, Agent, or Firm* — POLSINELLI PC

(57) ABSTRACT

The partial common path detection unit 12 configured to detect a common part exclusively in a portion between a start point and an end point of a path among a plurality of disease pathways representing, as a route map, an intermolecular interaction of related molecules with respect to a disease for each of a plurality of diseases related to state changes, and the common difference information provision unit 13 configured to provide information on a detected partial common path or a molecule included in the partial common path and a non-partial common path other than the partial common path or a molecule included in the non-partial common path in a state where whether the partial common path is related or the non-partial common path is related is distinguishable are provided, and a change in pathway due to the state change of the disease can be understood by providing information so that which part is common and which part is not common between a start point and an end point of a path can be understood in a relationship between a disease pathway related to a disease before state (Continued)

change and a disease pathway related to the disease after the state change.

12 Claims, 5 Drawing Sheets

(56) References Cited

OTHER PUBLICATIONS

European Search Report issued Apr. 23, 2025 for corresponding European Application No. 23841175.5.
Kelley B. P. et al.: "PathBLAST: a tool for alignment of protein interaction networks",Nucleic Acids Research, vol. 32, No. Web Server, Jul. 1, 2004, pp. W83-W88 XP093269445.
Pinter R. Y. et al.: "Alignment of metabolic pathways", Bioinformatics, vol. 21, No. 16, Jun. 28, 2005, pp. 3401-3408 XP093269465.
Alberich R. et al.: "MP-Align: alignment of metabolic pathways",BMC Systems Biology, Biomed Central Ltd, LO, vol. 8 No. 1, May 20, 2014, p. 58 (16 pages) XP021188426.

* cited by examiner

Fig. 6

| DISEASE NAME | ENTIRE PATH |
|---|---|
| DISEASE A | **MOLECULE 1—MOLECULE 2**—MOLECULE 3—MOLECULE 4—MOLECULE 5—MOLECULE 6／MOLECULE 7 |
| DISEASE B | MOLECULE 20—**MOLECULE 1—MOLECULE 2**—MOLECULE 11—MOLECULE12—MOLECULE13—MOLECULE14／MOLECULE 15—MOLECULE16—MOLECULE17—MOLECULE18—MOLECULE 19 |

(a)

| DISEASE NAME | PARTIAL COMMON PATH | NON-PARTIAL COMMON PATH Upper | NON-PARTIAL COMMON PATH Lower |
|---|---|---|---|
| DISEASE A | MOLECULE 1—MOLECULE 2 | ——— | —MOLECULE3—MOLECULE4—MOLECULE5—MOLECULE6／MOLECULE 7 |
| DISEASE B | MOLECULE 1—MOLECULE 2 | MOLECULE 20— | —MOLECULE 11—MOLECULE12—MOLECULE13—MOLECULE14／MOLECULE 15—MOLECULE16—MOLECULE17—MOLECULE18—MOLECULE 19 |

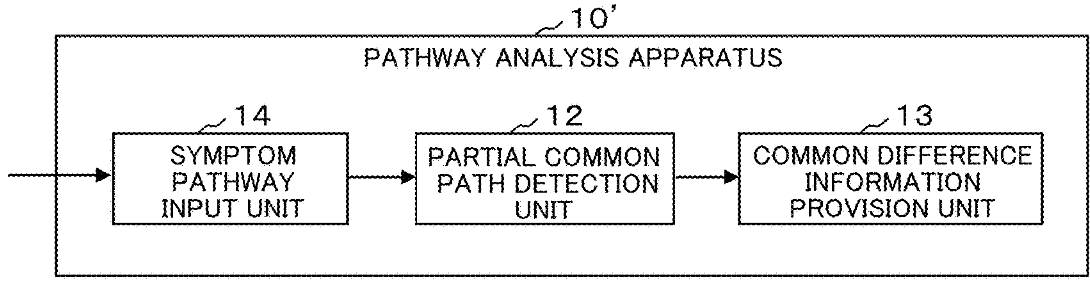

(a) DISEASE B (b) SYMPTOM RELATED TO DISEASE B

PATHWAY ANALYSIS APPARATUS, PATHWAY ANALYSIS METHOD, AND PATHWAY ANALYSIS PROGRAM

CROSS REFERENCE TO RELATED APPLICATIONS

This application is a National Phase filing under 35 U.S.C. § 371 of PCT/JP2023/023755 filed on Jun. 27, 2023; the entire contents of each application are hereby incorporated by reference.

TECHNICAL FIELD

The present invention relates to a pathway analysis apparatus, a pathway analysis method, and a pathway analysis program, and is particularly suitable for use in a technology for analyzing a pathway representing an intermolecular interaction as a route map.

BACKGROUND ART

Conventionally, there has been a known pathway (also referred to as an intermolecular network) representing an intermolecular interaction as a route map. The pathway represents a molecule of a gene, a protein, etc. using a symbol such as a circle or a square, and is expressed by connecting symbols with arrows that represent intermolecular interactions. Such visualization of the intermolecular interaction allows easier understanding of life phenomena such that it is possible to investigate a path containing a gene group whose expression level has changed. For example, a pathway is widely used in a field of disease treatment or drug discovery.

Note that there has been known technology for generating a molecular functional network in a necessary range by search and enabling estimation of a biological event directly or indirectly related to onset of any biomolecule (for example, see PTL 1). PTL 1 discloses that, by obtaining a part common to a plurality of molecular functional networks, a biomolecule appearing in a molecular functional network of the common part is estimated to be highly likely to play an important role in onset of a biological event.

Incidentally, even though a disease may be perceived as in a fixed state, there are various changes in the state in practice. For example, the changes in the state of the disease refer to changes such as development of hepatocellular carcinoma from liver cirrhosis (nonalcoholic fatty liver disease (NAFLD)→nonalcoholic steatohepatitis (NASH)→hepatocellular carcinoma (HCC)), or development of complications such as neuropathy, retinopathy, kidney damage and arteriosclerosis from diabetes.

Furthermore, even in the same disease, there are various state changes in symptoms. In other words, even though symptoms may be used to definitively diagnose a disease or serve as a treatment target, severity and continuity thereof vary even for the same disease. For example, in diabetic nephropathy, the state changes in symptoms include changes from microalbuminuria showing mild protein leakage, to albuminuria, and then severe and persistent proteinuria.

Conventionally, it has been difficult to perceive a state change of a disease or symptom as a change in an intermolecular network, and the scope of drug discovery target search utilizing an intermolecular network has been limited. Even though PTL 1 mentioned above discloses generating a necessary range of molecular functional networks using various search functions, there is no search function focusing on perceiving a state change of a disease or symptom as a change in an intermolecular network.

CITATION LIST

Patent Literature

PTL 1: WO2003/077159

SUMMARY OF INVENTION

Technical Problem

The present invention has been made to solve such a problem, and an object of the invention is to allow a state change of a disease or symptom to be perceived as a change in a pathway (an intermolecular network).

Solution to Problem

To solve the above-mentioned problem, in the invention, a common part is detected exclusively in a portion between a start point and an end point of a path among a plurality of disease pathways representing, as a route map, an intermolecular interaction of related molecules with respect to a disease for each of a plurality of diseases related to state changes or among a plurality of symptom pathways representing, as a route map, an intermolecular interaction of related molecules with respect to a symptom for each of a plurality of symptoms related to state changes, and information on a detected partial common path and a non-partial common path other than the partial common path is provided in a mutually distinguishable state.

Advantageous Effects of Invention

According to the invention configured as described above, information is provided so that which part is common and which part is not common between a start point and an end point of a path can be understood in a relationship between a disease pathway related to a disease before state change and a disease pathway related to a disease after the state change. Since a state change of a disease appears as a partial change between a start point and an end point of a path in a disease pathway, a change in pathway due to the state change of the disease can be understood by specifying a common part and a non-common part in the path before and after the state change of the disease.

In addition, according to the invention, information is provided so that which part is common and which part is not common between a start point and an end point of a path can be understood in a relationship between a symptom pathway related to a symptom before state change and a symptom pathway related to a symptom after the state change. Since a state change of a symptom appears as a partial change between a start point and an end point of a path in a symptom pathway, a change in pathway due to the state change of the symptom can be understood by specifying a common part and a non-common part in the path before and after the state change of the symptom.

BRIEF DESCRIPTION OF DRAWINGS

FIG. 6 is a diagram illustrating an example of information provision by a common difference information provision unit.

FIG. 7 is a block diagram illustrating another functional configuration example of a pathway analysis apparatus according to the first embodiment.

DESCRIPTION OF EMBODIMENTS

First Embodiment

Figure 1:
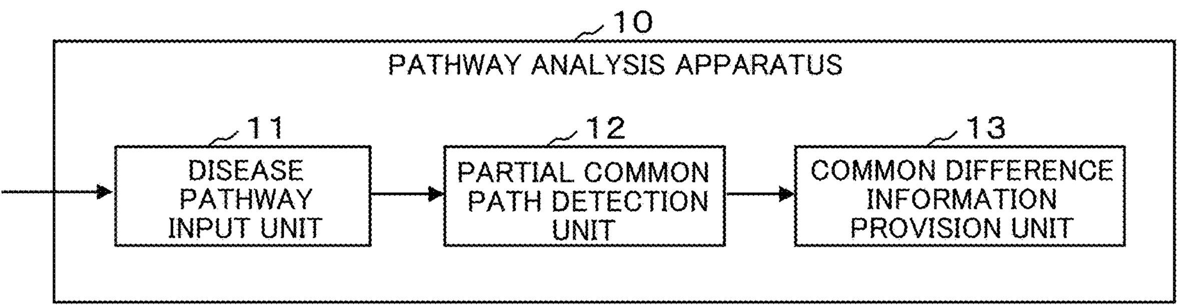
FIG. 1 is a block diagram illustrating a functional configuration example of a pathway analysis apparatus according to a first embodiment.

A first embodiment of the invention will be described below based on the drawings. FIG. 1 is a block diagram illustrating a functional configuration example of a pathway analysis apparatus 10 according to the first embodiment. As illustrated in FIG. 1, the pathway analysis apparatus 10 according to the first embodiment includes a disease pathway input unit 11, a partial common path detection unit 12, and a common difference information provision unit 13 as functional components.

The functional blocks 11 to 13 can be each configured by hardware, a DSP (Digital Signal Processor), or software. For example, the functional blocks 11 to 13 are realized by executing a program stored in a storage medium such as a RAM, a ROM, a hard disk, or a semiconductor memory under control of a microcomputer including a CPU, the RAM, the ROM, etc. Note that these functional blocks 11 to 13 illustrate a processing procedure of a pathway analysis method.

The disease pathway input unit 11 inputs a plurality of pathways (hereinafter referred to as disease pathways) generated for each of a plurality of diseases related to state changes. The plurality of diseases related to state changes are a combination of a plurality of diseases which is likely to progress from one disease to another disease, and are, for example, a combination of NAFLD, NASH, and HCC, a combination of diabetes, neuropathy, retinopathy, kidney damage, and arteriosclerosis, etc.

A disease pathway is an intermolecular network representing an intermolecular interaction of related molecules with respect to a disease as a route map. In other words, the disease pathway is a route map generated so that, among molecules (genes or proteins) related to the disease, a molecule whose property acting on the disease is causativeness (hereinafter referred to as a causative molecule) is disposed on an upstream side of a path, a molecule whose property acting on the disease is responsiveness (hereinafter referred to as a responsive molecule) is disposed on a downstream side of the path, and other molecules (hereinafter referred to as linking molecules) are disposed between the causative molecule and the responsive molecule. The causativeness is a property that may cause a disease due to the presence or mutation of the molecule. Responsiveness is a property that a molecule may mutate (change) due to the onset of a disease.

Here, when a disease pathway related to a specific disease is generated, it is possible to use known information recorded in various documents, databases, etc. as information on a plurality of molecules related to the disease and information on properties (causativeness or responsiveness) of the molecules acting on the disease. In addition, it is possible to use information obtained by estimating molecules related to a specific disease using a predetermined algorithm, and estimating properties of specific molecules acting on a disease using a predetermined algorithm.

Any algorithm can be used as an algorithm for estimating a related molecule or an algorithm for estimating a property of a molecule. For example, it is possible to estimate a new molecule related to a disease using an estimation model machine-learned using known information for relevance between a disease and a molecule. Furthermore, it is possible to estimate a new property of a molecule using an estimation model machine-learned using known information for a property of a molecule acting on a disease.

The disease pathway may be manually created using a related molecule obtained from known information and/or a related molecule estimated by a predetermined algorithm, or may be generated by computer processing. When a disease pathway is generated by computer processing, also any algorithm can be used as an algorithm for generating a pathway by connecting a causative molecule, a responsive molecule, and a linking molecule.

For example, it is possible to generate a pathway by optimization processing utilizing a minimum flow algorithm using a property of each molecule and known information indicating an intermolecular connection relationship. Here, the intermolecular connection relationship includes, for example, a relationship in which when an expression level of a certain molecule increases (or decreases), an expression level of another molecule increases (decreases) in conjunction with the increase (decrease).

Note that, for example, an algorithm described in JP6915818B can be used as a generation algorithm of the disease pathway. In this case, the disease pathway input unit 11 inputs a plurality of disease pathways generated by the algorithm described in JP6915818B for each of a plurality of diseases related to state changes.

Figure 2:
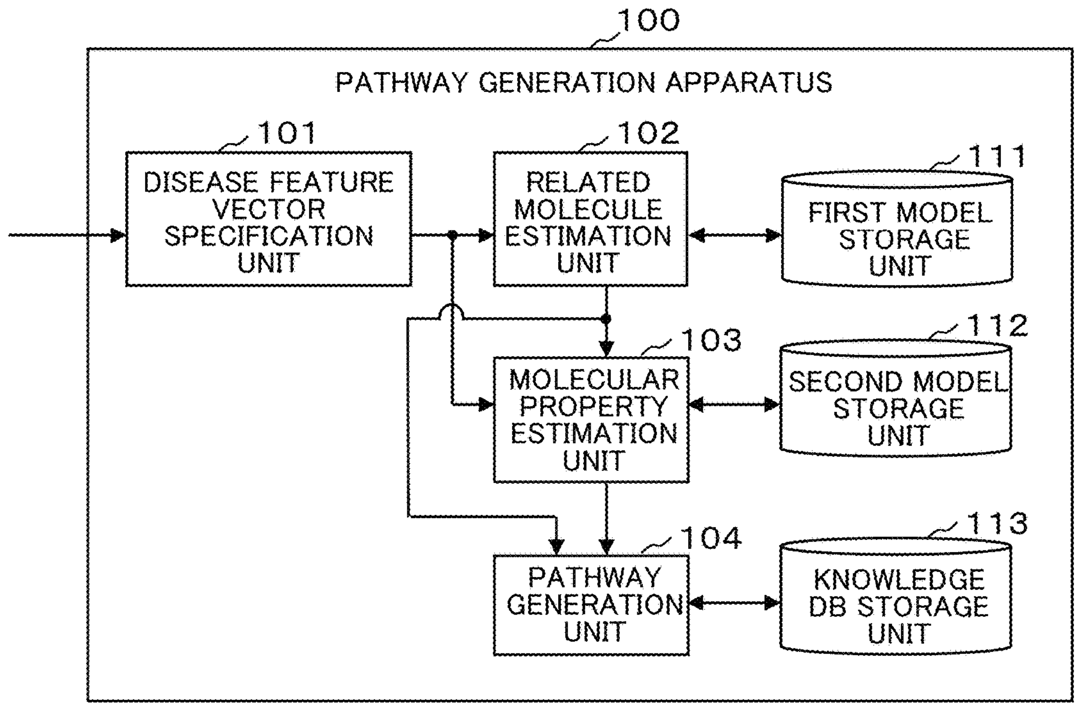
FIG. 2 is a block diagram illustrating a functional configuration example of a pathway generation apparatus.

A pathway generation method described in JP6915818B will be briefly described below. FIG. 2 is a block diagram illustrating a functional configuration example of a pathway generation apparatus 100.

The disease feature vector specification unit 101 specifies a feature vector (hereinafter referred to as a disease feature vector) corresponding to the disease name. The disease feature vector is data representing features of the disease (features that can identify the disease) as a combination of values of a plurality of elements. As an example, a vector representing a text to which a disease name included as a word in a plurality of texts contributes and a degree at which the disease name contributes to the text is used as a disease feature vector.

While a disease name as a word tends to be used in a text describing a disease, the disease name tends not to be used in a text unrelated to the disease. In addition, among texts describing a disease, a text containing a certain disease name as a word is a text describing the disease, and it is highly possible that the disease name is not included in a text describing another type of disease. That is, a text containing a disease name as a word tends to differ depending on the type of disease which is a theme of the text. Therefore, a vector representing a text to which a disease name contributes and a degree at which the disease name contributes to the text may be used as a feature vector that can identify a disease.

Figure 3:
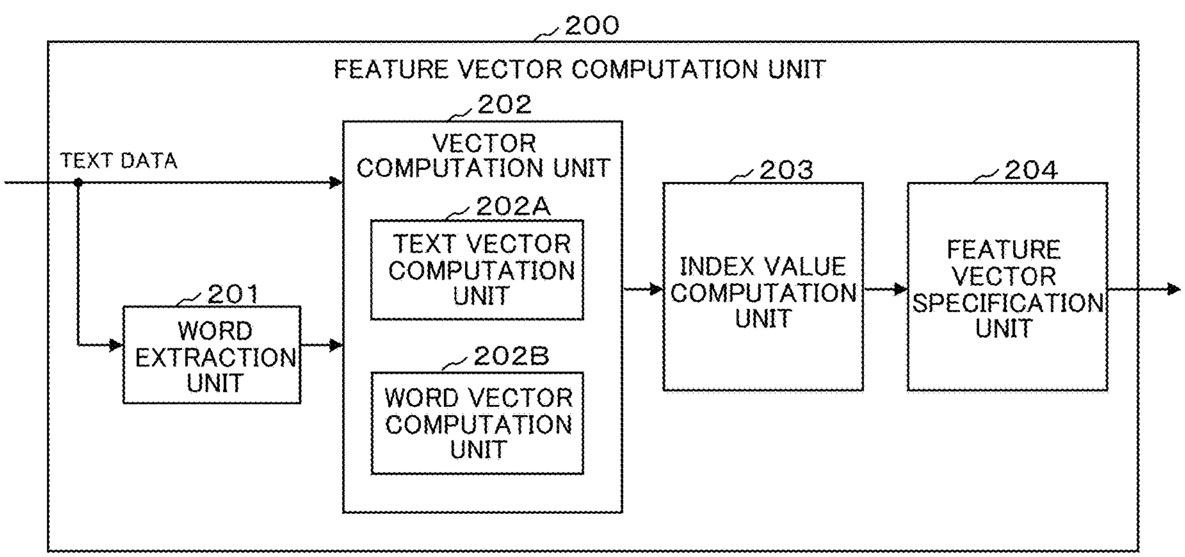
FIG. 3 is a block diagram illustrating a functional configuration example of a feature vector computation apparatus.

For example, such a disease feature vector is calculated by a feature vector computation apparatus 200 illustrated in FIG. 3. The feature vector computation apparatus 200 illustrated in FIG. 3 inputs text data related to a text and calculates and outputs a disease feature vector reflecting a relationship between the text and a word contained therein.

In FIG. 3, the word extraction unit 201 analyzes m texts (m is an arbitrary integer of 2 or more) and extracts n words (n is an arbitrary integer of 2 or more) from the m texts. As a method of analyzing texts, for example, a known morphological analysis can be used. Note that the same word may be included in the m texts a plurality of times. In this case, the word extraction unit 201 does not extract the plurality of the same words, and extracts only one. That is, the n words extracted by the word extraction unit 201 refer to n types of words.

The vector computation unit 202 computes m text vectors and n word vectors from the m texts and the n words. Here, the text vector computation unit 202A converts each of the m texts to be analyzed by the word extraction unit 201 into a q-dimensional vector (q is an arbitrary integer of 2 or more) according to a predetermined rule, thereby computing the m text vectors $d_i$ (i=1, 2, . . . , m) (hereinafter, the symbol "→" indicates a vector) including q axis components. In addition, the word vector computation unit 202B converts each of the n words extracted by the word extraction unit 201 into a q-dimensional vector according to a predetermined rule, thereby computing the n word vectors $w_j$ (j=1, 2, . . . , n) including q axis components. A detailed description of a method of calculating the text vectors $d_i$→ and the word vectors $w_j$→ will be omitted here.

The index value computation unit 203 takes each of the inner products of the m text vectors $d_i$→and the n word vectors $w_j$→ computed by the vector computation unit 202, thereby computing index values reflecting the relationship between the m texts $d_i$ and the n words $w_j$. Here, as shown in the following Equation (1), the index value computation unit 203 obtains the product of a text matrix D having the respective q axis components ($d_{11}$ to $d_{mq}$) of the m text vectors $d_i$→as respective elements and a word matrix W having the respective q axis components ($w_{11}$ to $w_{nq}$) of the n word vectors $w_j$→as respective elements, thereby computing an index value matrix DW having m×n index values as elements. Here, $W^t$ is the transposed matrix of the word matrix.

[Equation 1]

$$D = \begin{pmatrix} d_{11} & d_{12} & \dots & d_{1q} \\ d_{21} & d_{22} & \dots & d_{2q} \\ \vdots & \vdots & \ddots & \vdots \\ d_{m1} & d_{m2} & \dots & d_{mq} \end{pmatrix} \quad W = \begin{pmatrix} w_{11} & w_{12} & \dots & w_{1q} \\ w_{21} & w_{22} & \dots & w_{2q} \\ \vdots & \vdots & \ddots & \vdots \\ w_{n1} & w_{m2} & \dots & w_{mq} \end{pmatrix} \tag{1}$$

$$DW = D * W^t = \begin{pmatrix} dw_{11} & dw_{12} & \dots & dw_{1n} \\ dw_{21} & dw_{22} & \dots & dw_{2n} \\ \vdots & \vdots & \ddots & \vdots \\ dw_{m1} & dw_{m2} & \dots & dw_{mn} \end{pmatrix}$$

Each element of the index value matrix DW computed in this manner may indicate which word contributes to which text and to what extent and which text contributes to which word and to what extent. For example, an element $dw_{12}$ in the first row and the second column may be a value indicating a degree at which the word $w_2$ contributes to a text $d_i$ and may be a value indicating a degree at which the text $d_i$ contributes to a word $w_2$. In this way, each row of the index value matrix DW can be used to evaluate the similarity of a text, and each column can be used to evaluate the similarity of a word.

Figure 4:
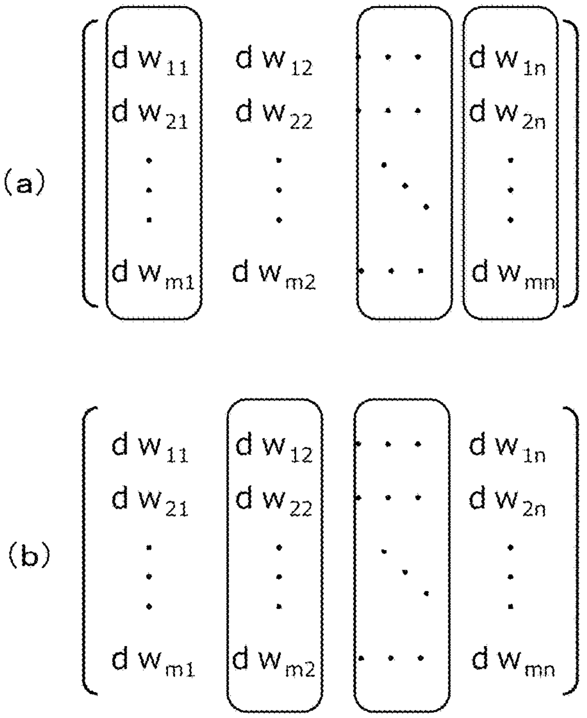
FIG. 4 is a diagram illustrating an example of a disease feature vector and a molecule feature vector.

The feature vector specification unit 204 specifies, as a disease feature vector, a word index value group including m index values for one disease name for each of a plurality of disease names among n words. That is, as illustrated in FIG. 4(*a*), the feature vector specification unit 204 specifies, as a disease feature vector corresponding to each disease name, a word index value group related to a word corresponding to a disease name among n sets of word index value groups (m index values per column) constituting respective columns of the index value matrix DW.

Returning to FIG. 2, a configuration of the pathway generation apparatus 100 will be described. The related molecule estimation unit 102 inputs a disease feature vector specified by the disease feature vector specification unit 101 to a first trained model stored in advance in the first model storage unit 111, thereby estimating a plurality of molecules associated with the disease. Here, the first trained model is subjected to machine learning so as to output information about a molecule corresponding to the molecule feature vector similar to the disease feature vector when the disease feature vector is input based on a similarity between the disease feature vector and the molecule feature vector.

The molecule feature vector used here is data representing a feature (feature that can identify a molecule) of a molecule of a protein, a gene, etc. as a combination of values of a plurality of elements. As an example, a vector representing a text to which a molecule name included as a word in a plurality of texts contributes and a degree at which the molecule name contributes to the text is used as a molecule feature vector. Also this molecule feature vector can be computed by the feature vector computation apparatus 200 illustrated in FIG. 3.

That is, the feature vector specification unit 204 specifies, as a molecule feature vector, a word index value group including m index values for one molecule name for each of a plurality of molecule names among n words. Specifically, as illustrated in FIG. 4(*b*), the feature vector specification unit 204 specifies, as a molecule feature vector corresponding to each molecule name, a word index value group related to a word corresponding to a molecule name among n sets of word index value groups (m index values per column) constituting respective columns of the index value matrix DW.

The feature vector computation apparatus 200 computes a disease feature vector related to a plurality of disease names and computes a molecule feature vector related to a plurality of molecule names. Then, machine learning of the first trained model is performed in advance using these data sets, and the first trained model learned based on the similarity between the disease feature vector and the molecule feature vector is stored in the first model storage unit 111.

Here, the similarity between the disease feature vector and the molecule feature vector can be evaluated by various methods. For example, it is possible to apply a method of extracting a feature quantity using a predetermined function for each of the disease feature vector and the molecule feature vector and evaluating a similarity of the feature quantity. Alternatively, it is possible to use a Euclidean distance or cosine similarity between the word index value group of the disease feature vector and the word index value group of the molecule feature vector, or it is possible to use an edit distance.

The molecular property estimation unit 103 inputs a disease feature vector specified by the disease feature vector specification unit 101 and a molecule feature vector specified for a plurality of molecules estimated by the related molecule estimation unit 102 to the second trained model stored in the second model storage unit 112, thereby estimating a probability that a molecule acting on the disease is causative or responsive as a property for each of a plurality of molecules presumed to be associated with the disease.

Here, the second trained model is subjected to machine learning so as to output a probability that a property of a molecule is causative or responsive when a disease feature vector and a molecule feature vector are input using the disease feature vector, the molecule feature vector, and a data set of property information representing the property of the molecule acting on a disease as teacher data.

The pathway generation unit 104 generates a pathway (an intermolecular network) representing an intermolecular interaction as a route map in a manner that a causative molecule is on an upstream side and a responsive molecule is on an downstream side and that an intermolecular connection relationship shown by a known knowledge database is reflected for a plurality of molecules whose relevance to the disease is estimated by the related molecule estimation unit 102 by using a property of a molecule estimated by the molecular property estimation unit 103 and the knowledge database showing the intermolecular connection relationship.

In this instance, for example, the pathway generation unit 104 uses a minimum flow algorithm to generate the pathway in a manner that the causative molecule whose probability value estimated to be causative by the molecular property estimation unit 103 is larger than a first threshold Th1 is disposed on the upstream side of the pathway, the responsive molecule whose probability value is smaller than a second threshold Th2 (Th1>Th2) is disposed on the downstream side of the pathway, and the linking molecule whose probability value is larger than or equal to the second threshold Th2 and smaller than or equal to the first threshold Th1 is disposed between the causative molecule and the responsive molecule.

The above description is an outline of the pathway generation method described in JP6915818B.

A description will be given by returning to FIG. 1. Among a plurality of disease pathways input by the disease pathway input unit 11, the partial common path detection unit 12 detects a common part only in a portion between a start point and an end point of a path. For example, the partial common path detection unit 12 divides the path from the start point to the end point into an upstream section, a midstream section, and a downstream section, and detects a part common to the plurality of disease pathways only in any of the divided sections. Such a partially common path is referred to as a partial common path.

As an example, two stages or three stages counting downstream from the start point of the path are set to the upstream section, two stages or three stages counting upstream from the end point of the path are set to the downstream section, and a part between the upstream section and the downstream section is set to the midstream section. For example, a user can designate a divided section in which the partial common path is detected among the upstream section, the midstream section, and the downstream section. Alternatively, the partial common path detection unit 12 may detect the partial common path in each of the upstream section, the midstream section, and the downstream section.

Figure 5:
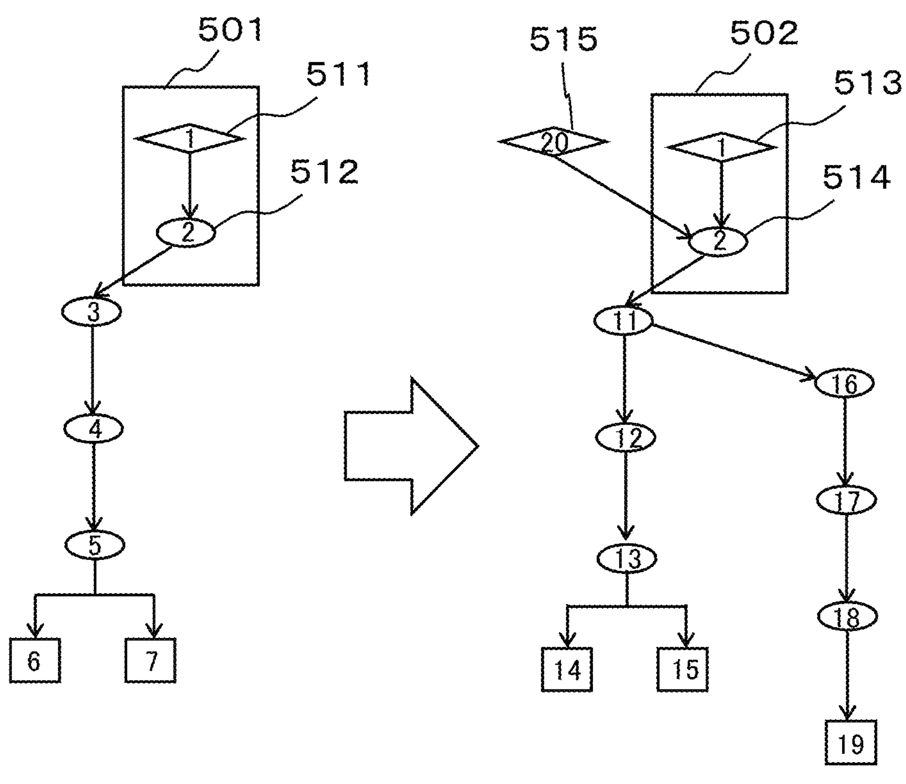
FIG. 5 is a diagram illustrating an example in which a partial common path is detected in an upstream section by a partial common path detection unit.

FIG. 5 is a diagram illustrating an example in which two stages counting downstream from a start point of a path are set to an upstream section, and a partial common path is detected in the upstream section. To simplify description, only a part of the path included in the entire pathway (intermolecular network) is illustrated here. In the pathway (part of the whole) illustrated in FIG. 5, a diamond-shaped node indicates a causative molecule, a rectangular node indicates a responsive molecule, and an oval-shaped node indicates a linking molecule. A number attached to each node is provisionally written as an identifier of each molecule, and nodes having the same number indicate the same molecule.

FIG. 5(*a*) illustrates a disease pathway related to a disease A before state change (for example, NASH), and FIG. 5(*b*) illustrates a disease pathway related to a disease B after state change (for example, HCC). A partial path 501 in an upstream section illustrated in FIG. 5(*a*) and a partial path 502 in an upstream section illustrated in FIG. 5(*b*) are partial common paths common to the two disease pathways. That is, two molecules 511 and 512 included in the partial path 501 illustrated in FIG. 5(*a*) and two molecules 513 and 514 included in the partial path 502 illustrated in FIG. 5(*b*) are the same. In the disease pathway of the disease A illustrated in FIG. 5(*a*), a portion other than the partial common path 501 is a non-partial common path. Furthermore, in the disease pathway of the disease B illustrated in FIG. 5(*b*), a portion other than the partial common path 502 is a non-partial common path.

In FIG. 5(*b*), even though a causative molecule 515 is present in a first layer, and a path is connected from the causative molecule 515 to a linking molecule 514 in a second layer, such a path is not present in FIG. 5(*a*), and thus is not detected as a partial common path. Furthermore, when processing is performed to detect a partial common path by designating an upstream section, even when a partial common path is present in a midstream section or a downstream section, the partial common path is not detected by the partial common path detection unit 12.

Note that the partial common path detection unit 12 may detect a common part in a portion at any position from the start point to the end point of the path without dividing the path into the upstream section, the midstream section, and the downstream section. However, the common part to be detected is limited to a predetermined length or less (for example, a length common to two or three layers).

The common difference information provision unit 13 provides information on the partial common path detected by the partial common path detection unit 12 and a non-partial common path other than the partial common path in a mutually distinguishable state (hereinafter referred to as a state in which a common difference is distinguishable).

For example, as illustrated in FIG. 5, the common difference information provision unit 13 can display a pathway in a graph format on a display, and can display a partial common path in a state where the partial common path is distinguishable from other non-partial common paths. As an example of the distinguishable state, as illustrated in FIG. 5, the partial common paths 501 and 502 can be each surrounded by a rectangular frame. Alternatively, the partial common paths 501 and 502 may be highlighted or emphasized, or the partial common paths 501 and 502 may be displayed in a different color from that of the non-partial common paths.

In the case of the example illustrated in FIG. 5, a change occurs in a path from the midstream to the downstream due to addition of a causative molecule 515 to the disease pathway related to the disease A before the state change as a stimulus to the linking molecule 514 in the second layer, and as a result, it is possible to estimate that the disease A may have progressed to the disease B. In this case, for example, it is possible to recognize the causative molecule 515 as a drug discovery target molecule candidate.

As another example of an information provision method, as illustrated in FIG. 6, the common difference information provision unit 13 may output a pathway in a spreadsheet format or a text format, and allow a partial common path to be in a state where the partial common path is distinguishable from other non-partial common paths. As an example of the distinguishable state in this case, as illustrated in FIG. 6(*a*), a molecule name included in the partial common path in the entire path from the start point to the end point may be emphasized, or may be in a different color from that of other molecule names. In place thereof or in addition thereto, as illustrated in FIG. 6(*b*), molecule names included in the partial common path and molecule names included in the non-partial common path may be separately expressed.

Note that, as described above, even though FIG. 5 only illustrates paths including partial common paths, another path not including any partial common path is present in a pathway input by the disease pathway input unit 11. The common difference information provision unit 13 may provide information on a partial common path and a non-partial common path only for a path including a partial common path. That is, information on other paths not including any partial common path does not have to be provided.

As described in detail above, in the present embodiment, a common part is detected only in a portion between a start point and an end point of a path among a plurality of disease pathways generated for each of a plurality of diseases related to state changes, and information is provided so that the detected partial common path and a non-partial common path other than the partial common path are distinguishable from each other.

According to the present embodiment configured in this way, information is provided so that which part is common and which part is not common between a start point and an end point of a path can be understood in a relationship between a disease pathway related to a disease before state change and a disease pathway related to a disease after the state change. Since a state change of a disease appears as a partial change between a start point and an end point of a path in a pathway, a change in pathway due to the state change of the disease can be understood by specifying a common part and a non-common part in the path before and after the state change of the disease.

In addition, by designating the upstream section, the midstream section, and the downstream section to detect a partial common path, it is possible to perform analysis focusing on desired information. For example, when the upstream section is designated to detect a partial common path, it is possible to select a target molecule candidate that may cause changes in responsiveness (disease expression system) in diseases related to two state changes. In addition, when the downstream section is designated to detect a partial common path, even when responsiveness appears to be the same at a glance in diseases related to two state changes, it is possible to extract a difference in cause (stimulus) and analyze causes of the state changes due to the diseases. Furthermore, by designating the midstream section to detect a partial common path, it is possible to analyze factors related to differences in both causality and responsiveness.

Further, in the embodiment, a description has been given of an example in which the feature vector computed by the feature vector computation apparatus 200 illustrated in FIG. 3 is used as the disease feature vector and the molecule feature vector. However, the invention is not limited thereto. For example, in case that a vector represents a text to which a disease name or a molecule name contained as a word in a plurality of texts contributes and a degree at which the disease name or the molecule name contributes to the text, the vector is not limited to the feature vector computed by the feature vector computation apparatus 200 illustrated in FIG. 3. In addition, the feature vector may not be obtained from a relationship between a text and a word. When the feature of the disease or the molecule can be identified, the vector may be used as the disease feature vector or the molecule feature vector.

In the first embodiment described above, a description has been given of an example in which a partial common path is detected from a disease pathway expressing an intermolecular interaction of related molecules with respect to a disease as a route map. However, a partial common path may be detected from a pathway expressing an intermolecular interaction of related molecules with respect to a symptom as a route map (hereinafter referred to as a symptom pathway).

FIG. 7 is a block diagram illustrating functional configuration example of a pathway analysis apparatus 10' in this case. In FIG. 7, since components denoted by the same reference numerals as those illustrated in FIG. 1 have the same functions, a redundant description will be omitted here. The pathway analysis apparatus 10' illustrated in FIG. 7 includes a symptom pathway input unit 14 in place of the disease pathway input unit 11 as a functional configuration.

The symptom pathway input unit 14 inputs a plurality of disease pathways generated for each of a plurality of symptoms related to state changes. The plurality of symptoms related to state changes is a combination of a plurality of symptoms which is likely to progress from one symptom to another symptom with regard to the same disease, and is, for example, a combination of microalbuminuria, albuminuria, and severe and persistent proteinuria for diabetic nephropathy, etc.

The symptom pathway is an intermolecular network generated so that, among molecules related to a specific symptom, a molecule whose property acting on the symptom is causative is disposed on an upstream side of a path, a molecule whose property acting on the symptom is responsive is disposed on a downstream side of the path, and other molecules are disposed between the causative molecule and the responsive molecule. The symptom pathway can be generated using the same algorithm as that of the disease pathway.

Note that, when the symptom pathway is generated using the same algorithm as that of the disease pathway, a symptom feature vector is calculated using a symptom name included as a word in a plurality of texts. The symptom name used here is not limited to the case where the symptom name is associated with only a certain specific disease, and the symptom name may be associated with a plurality of different diseases (for example, edema is discussed in kidney and liver diseases, and proteinuria or decreased renal function is discussed in various renal and cardiac diseases).

When configured as in FIG. 7, information is provided so that which part is common and which part is not common between a start point and an end point of a path can be understood in a relationship between a symptom pathway related to a symptom before state change and a symptom pathway related to a symptom after the state change. Since a state change of a symptom appears as a partial change between a start point and an end point of a path in a pathway, a change in pathway due to the state change of the symptom can be understood by specifying a common part and a non-common part in the path before and after the state change of the symptom.

Second Embodiment

Figure 8:
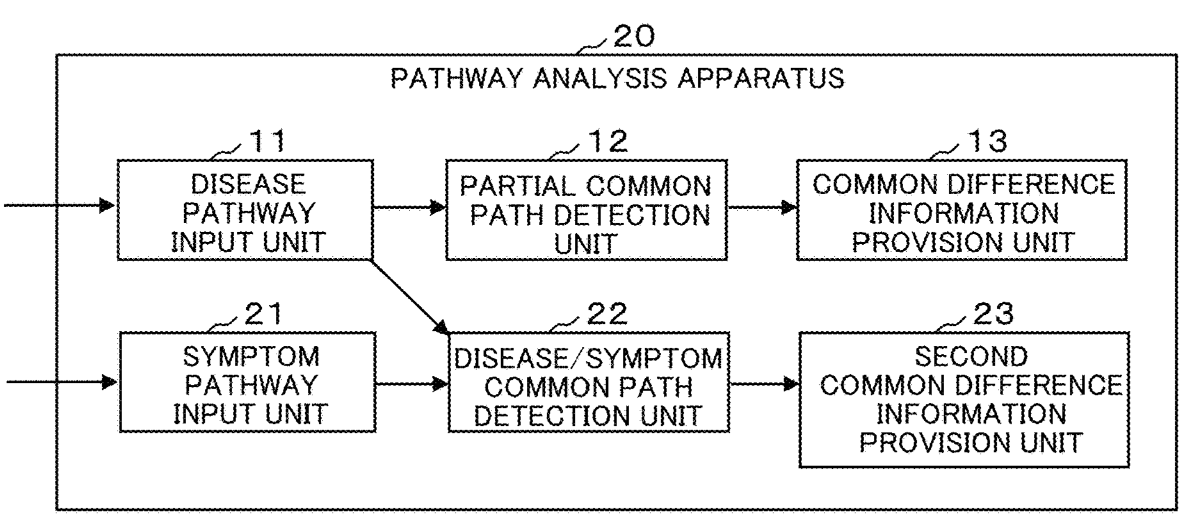
FIG. 8 is a block diagram illustrating a functional configuration example of a pathway analysis apparatus according to a second embodiment.

A second embodiment of the invention will be described below based on the drawings. FIG. 8 is a block diagram illustrating a functional configuration example of a pathway analysis apparatus 20 according to the second embodiment. In FIG. 8, since components denoted by the same reference numerals as those illustrated in FIG. 1 have the same functions, a redundant description will be omitted here.

As illustrated in FIG. 8, the pathway analysis apparatus 20 according to the second embodiment includes the disease pathway input unit 11, the partial common path detection unit 12, the common difference information provision unit 13, a symptom pathway input unit 21, a disease/symptom common path detection unit 22, and a second common difference information provision unit 23 as functional components.

The functional blocks 11 to 13 and 21 to 23 can be each configured by hardware, a DSP, or software. For example, the functional blocks 11 to 13 and 21 to 23 are realized by executing a program stored in a storage medium such as a RAM, a ROM, a hard disk, or a semiconductor memory under control of a microcomputer including a CPU, the RAM, the ROM, etc.

The symptom pathway input unit 21 inputs a symptom pathway expressing an intermolecular interaction of related molecules with respect to a symptom related to a disease as a route map. Here, the disease is some or all of a plurality of diseases related to state changes, and is a disease related to a disease pathway input by the disease pathway input unit 11. When there is a plurality of symptoms related to a disease, a symptom pathway generated for one of the symptoms may be input, or a symptom pathway generated for each of the plurality of symptoms may be input.

The disease/symptom common path detection unit 22 detects a common path between a disease pathway input by the disease pathway input unit 11 and a symptom pathway input by the symptom pathway input unit 21. Similarly to the partial common path detection unit 12, the disease/symptom common path detection unit 22 may detect a common part only in a portion between the start point and the end point of the path, and may detect a common part without being limited to the portion.

Here, the disease/symptom common path detection unit 22 detects a common path between a disease pathway related to the disease A before the state change and a symptom pathway associated with a symptom related to the disease A. Furthermore, the disease/symptom common path detection unit 22 detects a common path between a disease pathway related to the disease B after the state change and a symptom pathway associated with a symptom related to the disease B.

The second common difference information provision unit 23 provides information in a state where a common path detected by the disease/symptom common path detection unit 22 and a non-common path other than the common path are mutually distinguishable from each other (a state where a common difference is distinguishable). A method of providing information may be the same as that of the common difference information provision unit 13, and may be in a graph format, a spreadsheet format, or a text format.

Figure 9:
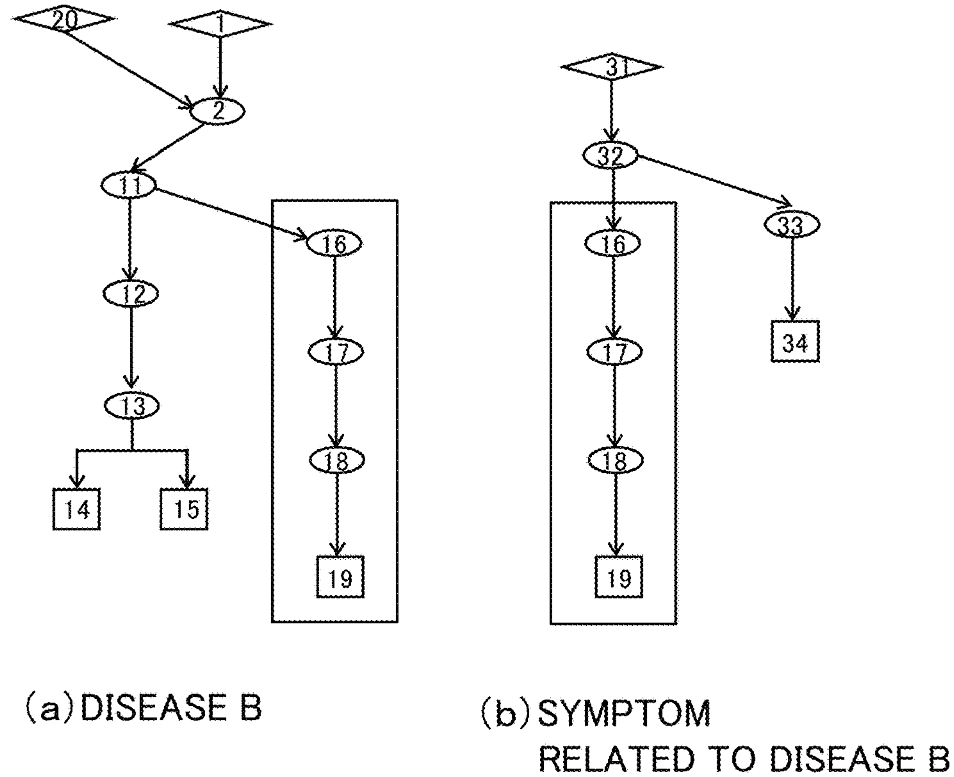
FIG. 9 is a diagram illustrating an example in which a common path is detected by a disease/symptom common path detection unit.

FIG. 9 is a diagram illustrating an example in which a common path is detected by the disease/symptom common path detection unit 22. Here, to simplify description, only paths in a portion included in the entire pathway are illustrated. FIG. 9(*a*) illustrates a disease pathway related to the disease B, and FIG. 9(*b*) illustrates a symptom pathway associated with one symptom related to the disease B. Paths surrounded by rectangular frames in FIGS. 9(*a*) and 9(*b*) are common paths between the disease pathway and the symptom pathway.

As described above with regard to the second embodiment, by detecting a common path between a disease pathway and a symptom pathway and providing information in a state where a common difference is distinguishable, it becomes possible to find out which path in the disease pathway is associated with the symptom pathway, or which path in the symptom pathway is associated with the disease pathway.

In this way, it is possible to specify which connection in a disease network deeply contributes to which symptom onset, and to specify which connection in a symptom network deeply contributes to which disease. In addition, since a common path between a disease pathway and a symptom pathway may appear as a commonality from a start point to an end point, it is possible to understand an important path universally involved in symptom onset causing onset of a symptom specific to a disease.

Note that the second common difference information provision unit 23 may represent a disease pathway in a state in which a common path and a non-common path with respect to a symptom pathway detected by the disease/symptom common path detection unit 22 are mutually distinguishable from each other, and output a graph, a spreadsheet, or text representing a partial common path and a non-partial common path detected by the partial common path detection unit 12 in a mutually distinguishable state.

In addition, the disease/symptom common path detection unit 22 may focus on a partial common path or a non-partial common path detected by the partial common path detection unit 12 with regard to a disease pathway, and detect a common path between the partial common path or the non-partial common path and a symptom pathway. In this way, it is possible to analyze a relationship between a disease and a symptom by focusing on a part considered to be a feature in a state change of the disease.

Note that, all the embodiments are merely examples of embodiment in carrying out the invention, and the technical scope of the invention should not be construed in a limited manner by the embodiments. That is, the invention can be implemented in various forms without departing from a gist or a main feature thereof.

REFERENCE SIGNS LIST

- 10, 10': pathway analysis apparatus
- 11: disease pathway input unit
- 12: partial common path detection unit
- 13: common difference information provision unit
- 14: symptom pathway input unit
- 20: pathway analysis apparatus
- 21: symptom pathway input unit
- 22: disease/symptom common path detection unit
- 23: second common difference information provision unit

The invention claimed is:

1. A pathway analysis apparatus characterized by comprising:

a partial common path detection unit configured to use three or more disease pathways related to state changes for disease pathways consisting of graph structure data representing related molecules with respect to a disease as nodes and representing an intermolecular interaction of the related molecules as edges connecting every two of the nodes or use three or more symptom pathways related to state changes for symptom pathways consisting of graph structure data representing related molecules with respect to a symptom as nodes and representing an intermolecular interaction of the related molecules as edges connecting every two of the nodes, and detect a part where connections of the nodes and the edges are common, exclusively in a portion between a start point and an end point of a path, between the graph structure data with respect to each combination of two of the pathways in an order of the state changes; and a common difference information provision unit configured to generate drawing data in which a specific display attribute is given to a partial common path detected by the partial common path detection unit and thereby provide information on the partial common path and a non-partial common path other than the partial common path in a mutually distinguishable display state.

2. The pathway analysis apparatus according to claim 1, characterized in that the partial common path detection unit divides the portion between the start point and the end point of the path into an upstream section, a midstream section, and a downstream section to exclusively use the graph structure data on any one of the divided sections, and detect a part where connections of the nodes and the edges are common among the plurality of disease pathways or a part where connections of the nodes and the edges are common among the plurality of symptom pathways.

3. The pathway analysis apparatus according to claim 1, characterized by further comprising:

a disease/symptom common path detection unit configured to detect a path where connections of the nodes and the edges are common between the graph structure data with respect to the disease pathways and the graph structure data with respect to the symptom pathways representing an intermolecular interaction of related molecules with respect to a symptom associated with the disease; and a second common difference information provision unit configured to generate drawing data in which a specific display attribute is given to a common path detected by the disease/symptom common path detection unit and thereby provide information on the common path and a non-common path other than the common path in a mutually distinguishable display state.

4. The pathway analysis apparatus according to claim 3, characterized in that the disease/symptom common path detection unit detects a path where connections of the nodes and the edges are common between the graph structure data with respect to the partial common path detected by the partial common path detection unit or the non-partial common path for the disease pathways and the graph structure data with respect to the symptom pathways.

5. The pathway analysis apparatus according to claim 1, characterized in that the disease pathways or the symptom pathways are graph structure data generated by optimization processing utilizing a minimum flow algorithm, by disposing a node representing a causative molecule whose property acting on a disease or a symptom is causativeness on an upstream side of a path, disposing a node representing a responsive molecule whose property acting on a disease or a symptom is responsiveness on a downstream side of the path, and disposing nodes representing linking molecules as the other molecules between the causative molecule and the responsive molecule.

6. A pathway analysis method characterized by comprising:

a step of using, by a partial common path detection unit of a pathway analysis apparatus, three or more disease pathways related to state changes for disease pathways consisting of graph structure data representing related molecules with respect to a disease as nodes and representing an intermolecular interaction of the related molecules as edges connecting every two of the nodes or using three or more symptom pathways related to state changes for symptom pathways consisting of graph structure data representing related molecules with respect to a symptom as nodes and representing an intermolecular interaction of the related molecules as edges connecting every two of the nodes, and detect a part where connections of the nodes and the edges are common, exclusively in a portion between a start point and an end point of a path, between the graph structure data with respect to each combination of two of the pathways in an order of the state changes; and a step of generating, by a common difference information provision unit of the pathway analysis apparatus, drawing data in which a specific display attribute is given to a partial common path detected by the partial common path detection unit and thereby providing information on the partial common path and a non-partial common path other than the partial common path in a mutually distinguishable display state.

7. A pathway analysis program stored on a non-transitory computer readable medium, the program for causing a computer to function as:

a partial common path detection means configured to use three or more disease pathways related to state changes for disease pathways consisting of graph structure data representing related molecules with respect to a disease as nodes and representing an intermolecular interaction of the related molecules as edges connecting every two of the nodes or use three or more symptom pathways related to state changes for symptom pathways consisting of graph structure data representing related molecules with respect to a symptom as nodes and representing an intermolecular interaction of the related molecules as edges connecting every two of the nodes, and detect a part where connections of the nodes and the edges are common, exclusively in a portion between a start point and an end point of a path between the graph structure data with respect to each combination of two of the pathways in an order of the state changes; and a common difference information provision means configured to generate drawing data in which a specific display attribute is given to a partial common path detected by the partial common path detection means and thereby provide information on the partial common path and a non-partial common path other than the partial common path in a mutually distinguishable display state.

8. The pathway analysis apparatus according to claim 2, characterized by further comprising:

a disease/symptom common path detection unit configured to detect a path where connections of the nodes and the edges are common between the graph structure data with respect to the disease pathways and the graph structure data with respect to the symptom pathways representing an intermolecular interaction of related molecules with respect to a symptom associated with the disease; and a second common difference information provision unit configured to generate drawing data in which a specific display attribute is given to a common path detected by the disease/symptom common path detection unit and thereby provide information on the common path and a non-common path other than the common path in a mutually distinguishable display state.

9. A pathway analysis apparatus characterized by comprising:

a partial common path detection unit configured to use a plurality of disease pathways related to state changes for disease pathways consisting of graph structure data representing related molecules with respect to a disease as nodes and representing an intermolecular interaction of the related molecules as edges connecting every two of the nodes or use a plurality of symptom pathways related to state changes for symptom pathways consisting of graph structure data representing related molecules with respect to a symptom as nodes and representing an intermolecular interaction of the related molecules as edges connecting every two of the nodes, and detect a part where connections of the nodes and the edges are common, exclusively in a portion between a start point and an end point of a path, between a plurality of the graph structure data; and a common difference information provision unit configured to generate drawing data in which a specific display attribute is given to a partial common path detected by the partial common path detection unit, the drawing data in which the plurality of disease pathways or the plurality of symptom pathways are visible simultaneously, and thereby provide information on the plurality of disease pathways or the plurality of symptom pathways in a display state where the partial common path and a non-partial common path other than the partial common path are mutually distinguishable and in a display state where the plurality of disease pathways or the plurality of symptom pathways can be compared to each other.

10. The pathway analysis apparatus according to claim 9, characterized in that the disease pathways or the symptom pathways are graph structure data generated by optimization processing utilizing a minimum flow algorithm, by disposing a node representing a causative molecule whose property acting on a disease or a symptom is causativeness on an upstream side of a path, disposing a node representing a responsive molecule whose property acting on a disease or a symptom is responsiveness on a downstream side of the path, and disposing nodes representing linking molecules as the other molecules between the causative molecule and the responsive molecule.

11. A pathway analysis method characterized by comprising:

a step of using, by a partial common path detection unit of a pathway analysis apparatus, a plurality of disease pathways related to state changes for disease pathways consisting of graph structure data representing related molecules with respect to a disease as nodes and representing an intermolecular interaction of the related molecules as edges connecting every two of the nodes or using a plurality of symptom pathways related to state changes for symptom pathways consisting of graph structure data representing related molecules with respect to a symptom as nodes and representing an intermolecular interaction of the related molecules as edges connecting every two of the nodes, and detect a part where connections of the nodes and the edges are common, exclusively in a portion between a start point and an end point of a path, between a plurality of the graph structure data; and a step of generating, by a common difference information provision unit of the pathway analysis apparatus, drawing data in which a specific display attribute is given to a partial common path detected by the partial common path detection unit, the drawing data in which the plurality of disease pathways or the plurality of symptom pathways are visible simultaneously, and thereby providing information on the plurality of disease pathways or the plurality of symptom pathways in a display state where the partial common path and a non-partial common path other than the partial common path are mutually distinguishable and in a display state where the plurality of disease pathways or the plurality of symptom pathways can be compared to each other.

12. A pathway analysis program stored on a non-transitory computer readable medium, the program for causing a computer to function as:

a partial common path detection means configured to use a plurality of disease pathways related to state changes for disease pathways consisting of graph structure data representing related molecules with respect to a disease as nodes and representing an intermolecular interaction of the related molecules as edges connecting every two of the nodes or use a plurality of symptom pathways related to state changes for symptom pathways consisting of graph structure data representing related molecules with respect to a symptom as nodes and representing an intermolecular interaction of the related molecules as edges connecting every two of the nodes, and detect a part where connections of the nodes and the edges are common, exclusively in a portion between a start point and an end point of a path, between a plurality of the graph structure data; and a common difference information provision means configured to generate drawing data in which a specific display attribute is given to a partial common path detected by the partial common path detection means, the drawing data in which the plurality of disease pathways or the plurality of symptom pathways are visible simultaneously, and thereby provide information on the plurality of disease pathways or the plurality of symptom pathways in a display state where the partial common path and a non-partial common path other than the partial common path are mutually distinguishable and in a display state where the plurality of disease pathways or the plurality of symptom pathways can be compared to each other.

* * * * *